(12) United States Patent
Bouthillier et al.

(10) Patent No.: US 9,226,789 B2
(45) Date of Patent: *Jan. 5, 2016

(54) THERMAL ABLATION SYSTEM

(71) Applicant: Boston Scientific Scimed, Inc., Maple Grove, MN (US)

(72) Inventors: Robert J. Bouthillier, Lincoln, RI (US); Michael P. Fusaro, Greenville, RI (US); Joseph M. Gordon, Providence, RI (US); Stephen S. Keaney, Groton, MA (US); Brian Maclean, Westford, MA (US); Andrew W. Marsella, Somerville, MA (US); David Robson, Providence, RI (US); Boris Shapeton, Natick, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 6 days.

This patent is subject to a terminal disclaimer.

(21) Appl. No.: 14/314,912

(22) Filed: Jun. 25, 2014

(65) Prior Publication Data

US 2014/0309630 A1  Oct. 16, 2014

Related U.S. Application Data

(63) Continuation of application No. 13/408,707, filed on Feb. 29, 2012, now Pat. No. 8,814,851, which is a
(Continued)

(51) Int. Cl.
*A61B 18/04* (2006.01)
*A61B 17/00* (2006.01)
(Continued)

(52) U.S. Cl.
CPC ....... *A61B 18/04* (2013.01); *A61B 2017/00199* (2013.01); *A61B 2017/4216* (2013.01); *A61B 2018/00035* (2013.01);
(Continued)

(58) Field of Classification Search
CPC ............... A61B 2017/00199; A61B 2018/046; A61B 18/04; A61B 2018/00035; A61B 2018/00577; A61M 3/0258; A61M 2205/12
USPC ..................... 604/65–67, 113; 606/27–29, 31
See application file for complete search history.

(56) References Cited

U.S. PATENT DOCUMENTS 5,891,094 A * 4/1999 Masterson ............. A61B 18/08
604/113
2003/0125721 A1 * 7/2003 Yon ........................ A61B 18/02
606/21

(Continued)

*Primary Examiner* — Nicholas Lucchesi
*Assistant Examiner* — Gerald Landry, II
(74) *Attorney, Agent, or Firm* — Fay Kaplun & Marcin, LLP

(57) ABSTRACT

A thermal ablation system comprises a fluid handling unit receiving fluid from a fluid source at a first pressure, the fluid handling unit including a heater heating the fluid to a desired temperature and a pump and an introducer including a sheath which, when in an operative position, is received within a hollow organ, the sheath including a delivery lumen introducing fluid heated by the heater to the hollow organ and a return lumen withdrawing fluid from the hollow organ and returning the withdrawn fluid to the console via a return lumen, wherein the pump increases a pressure of the fluid between the fluid source and the delivery lumen of the introducer.

20 Claims, 15 Drawing Sheets

Related U.S. Application Data continuation of application No. 12/270,401, filed on Nov. 13, 2008, now abandoned.

(60) Provisional application No. 60/987,913, filed on Nov. 14, 2007.

(51) Int. Cl.
  *A61B 17/42* (2006.01)
  *A61B 18/00* (2006.01)

(52) U.S. Cl.
  CPC .......... *A61B 2018/00559* (2013.01); *A61B 2018/00577* (2013.01); *A61B 2018/046* (2013.01)

(56) References Cited

U.S. PATENT DOCUMENTS

| | | | |
|---|---|---|---|
| 2006/0122673 A1* | 6/2006 | Callister | A61F 7/12 607/105 |
| 2007/0078370 A1* | 4/2007 | Shener | A61M 3/022 604/8 |
| 2007/0106247 A1* | 5/2007 | Burnett | A61F 7/12 604/508 |
| 2007/0161978 A1* | 7/2007 | Fedenia | A61B 18/1402 606/34 |
| 2008/0097563 A1* | 4/2008 | Petrie | A61B 18/04 607/105 |
| 2010/0222647 A1* | 9/2010 | Hashimshony | A61B 1/04 600/301 |

* cited by examiner

FIG. 11. Open-Loop (Priming, Cooling)

F I G. 12. Closed-Loop (Heating, Ablation)

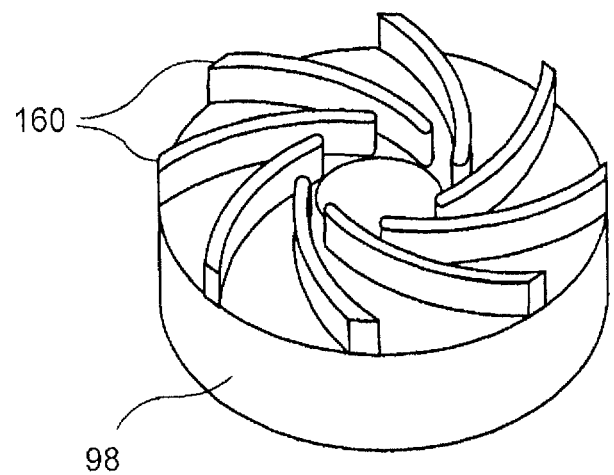
F I G. 14
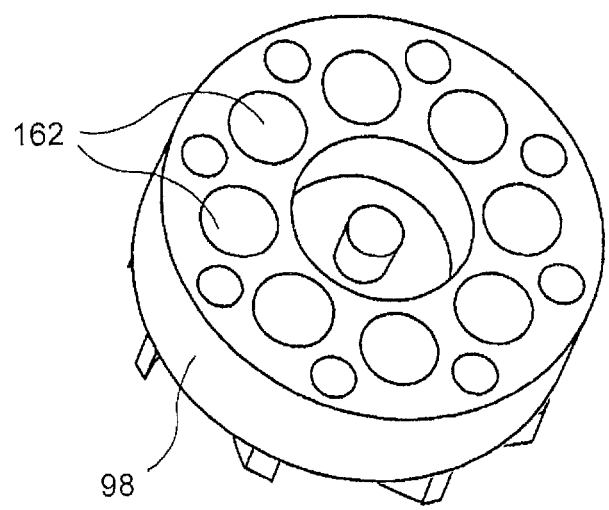
F I G. 15

THERMAL ABLATION SYSTEM

PRIORITY CLAIM

The present application is a Continuation of U.S. patent application Ser. No. 13/408,707 filed on Feb. 29, 2012, now U.S. Pat. No. 8,814,851; which is a Continuation of U.S. patent application Ser. No. 12/270,401 filed on Nov. 13, 2008; which claims the priority to the U.S. Provisional Application Ser. No. 60/987,913 filed on Nov. 14, 2007. The entire disclosure of these applications/patents are expressly incorporated herein by reference.

BACKGROUND

Menorrhagia, excessive uterine bleeding during a prolonged menstrual period, has been attributed to disorders of the endometrial lining of the uterus. While a hysterectomy provides a definitive treatment for menorrhagia, physicians and patients may choose less invasive procedures to reduce side effects, prolonged hospital stays and procedural and post-operative discomfort.

Generally, the less invasive procedures employ electrical energy (e.g., RF energy), heat (e.g., laser) or cryogenic treatment. However, these procedures typically rely on direct visualization of the uterus and an experienced operator applying the energy, heat, etc. to selected portions of the uterine lining. Alternatively, the entire inner lining of the uterus may be treated by conduction uterine ablation, i.e., circulating a heated fluid through the uterus. In other similar procedures, the heated fluid may be contained within a balloon while circulating through the uterus.

SUMMARY OF THE INVENTION

The present invention relates to a thermal ablation system comprising a fluid handling unit receiving fluid from a fluid source at a first pressure, the fluid handling unit including a heater heating the fluid to a desired temperature and a pump and an introducer including a sheath which, when in an operative position, is received within a hollow organ, the sheath including a delivery lumen introducing fluid heated by the heater to the hollow organ and a return lumen withdrawing fluid from the hollow organ and returning the withdrawn fluid to the console via a return lumen, wherein the pump increases a pressure of the fluid between the fluid source and the delivery lumen of the introducer.

BRIEF DESCRIPTION OF DRAWINGS

FIG. 14 shows an exemplary embodiment of an impeller of a thermal ablation system according to the present invention;

FIG. 15 shows an exemplary embodiment of an impeller of a thermal ablation system according to the present invention.

DETAILED DESCRIPTION

Figure 1:
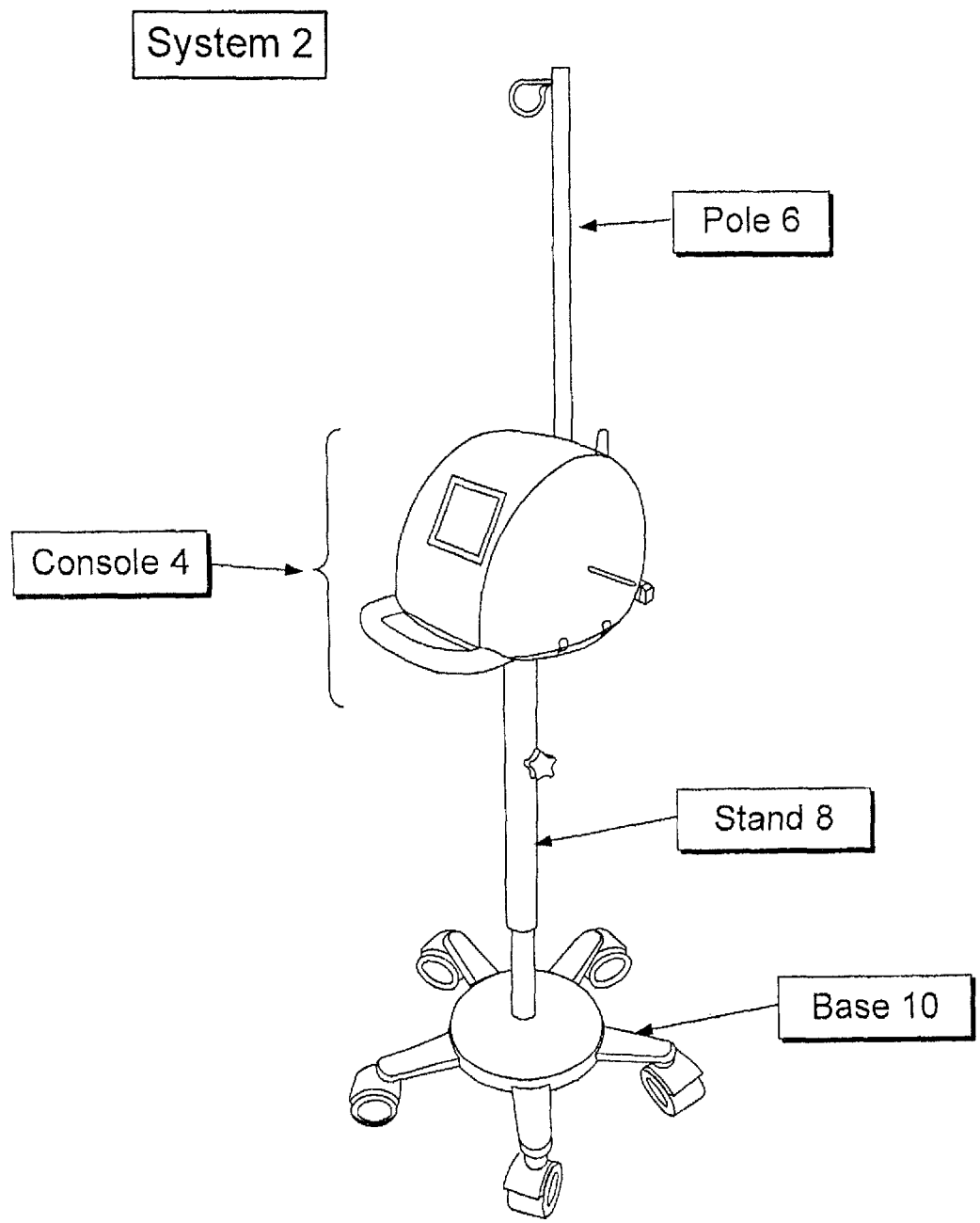
FIG. 1 shows an exemplary embodiment of a thermal ablation system according to the present invention.

The present invention may be further understood with reference to the following description and to the appended drawings, wherein like elements are referred to with the same reference numerals. The present invention relates to systems, methods and apparatuses for thermally ablating tissue, e.g., tissue lining an inner surface of a hollow organ. In particular, the present invention relates to devices for ablating the endometrial lining of the uterus. However, those of skill in the art will understand that the present invention, or components thereof, may be utilized in prostate treatment (microwave or cyroablation) systems, irrigation systems or other procedure which require infusion of fluid into a patient.

FIG. 1 shows an exemplary embodiment of a thermal ablation system 2 according to the present invention. Generally, the system 2 includes a console 4 having a pole 6 extending from an upper portion thereof and a stand 8 coupled to a lower portion thereof. The pole 6 preferably extends to a predetermined height above the console 4 so that an intravenous (IV) bag (not shown) hung therefrom will supply fluid to the console 4 at a desired pressure. The IV bag contains fluid such as saline that will be heated and circulated through the uterus to ablate the endometrial lining. During the ablation procedure, an operator (e.g., physician, nurse, etc.) may be required to substitute the IV bag for IV bags with other fluids depending on stage of the ablation procedure. For example, prior to the procedure an anesthetic fluid may be circulated through the uterus to numb the surgical site. Additionally, after the endometrial lining has been ablated, an analgesic and/or infection preventative solution may be circulated through the uterus. In another exemplary embodiment, IV bags for any fluids required during the procedure may be concurrently attached to the pole 6 with the height of the pole 6 determining the pressure at which these fluids will be supplied to the console 4.

A height of the stand 8 on which a fluid supply bag will be hung is preferably variable using a height-adjusting mechanism to control a pressure of fluid reaching the treatment site as will be described below. The height-adjusting mechanism may be a pneumatic lift, a frictional lock, etc., allowing the operator to manually adjust of the height of the stand 8. In another exemplary embodiment, the height-adjusting mechanism may comprise an automated height adjustment mechanism controlled by user actuation or automatically by electronic circuitry in the console 4 based on sensor data, etc.

In the exemplary embodiment, the stand 8 is provided with a mobile base 10 (e.g., locking wheels) so that the system 2 is easily moveable and steerable. However, those of skill in the art will understand that the base 10 may be static or that electronic control and movement of the system 2 may also be implemented.

Figure 2:
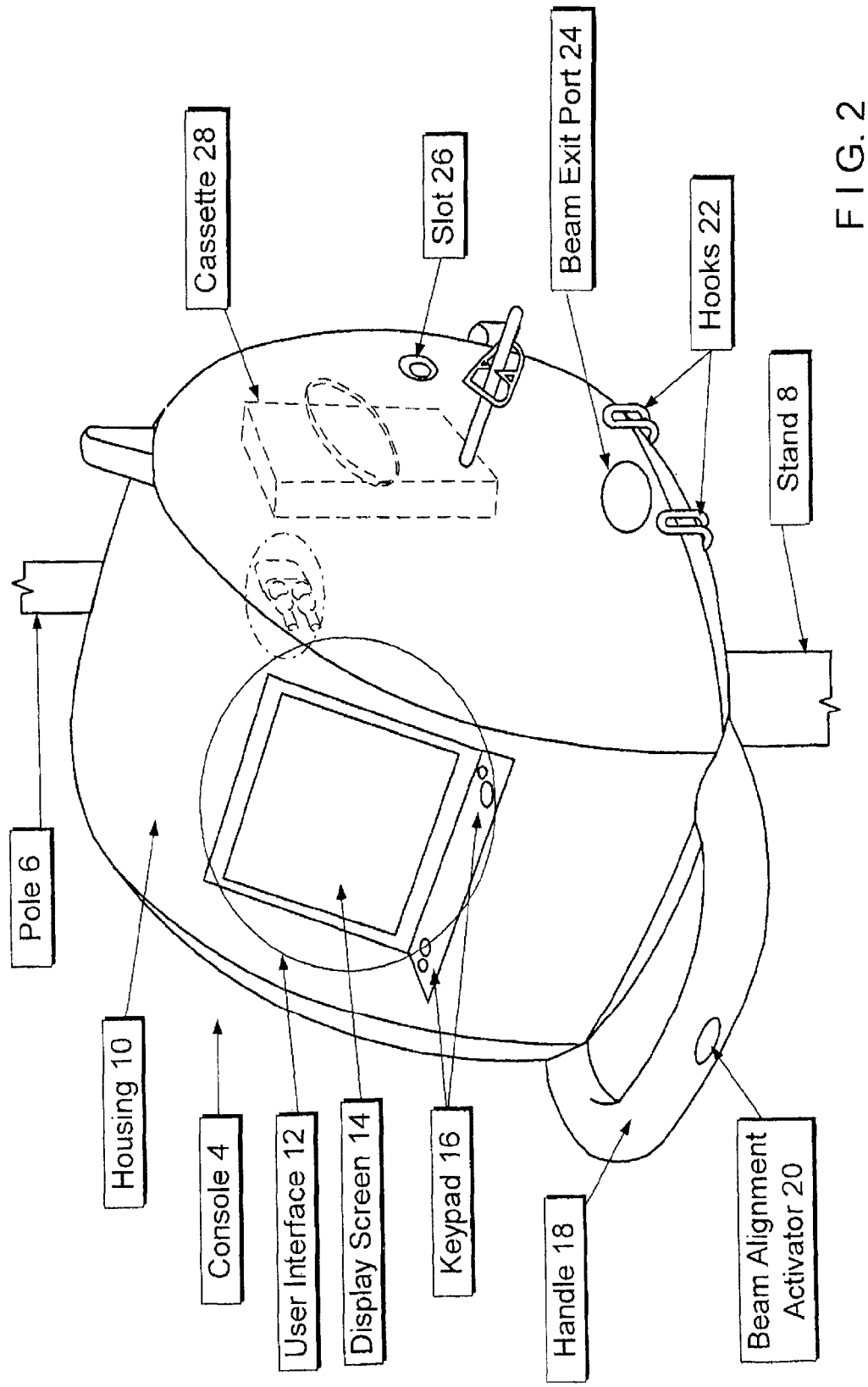
FIG. 2 shows a frontal view of an exemplary embodiment of a console of a thermal ablation system according to the present invention.

As shown in FIG. 2, the console 4 according to the present invention comprises a housing 10 encasing electronic circuitry and providing a user interface 12 for displaying content (e.g., instructions, procedural data, warnings, etc.) and receiving user input. The user interface 12 may comprise a display screen 14 (e.g., LCD) and a keypad 16 for submitting input to the console 4. Those of skill in the art will understand that the keypad 16 may be replaced or augmented by dials, switches, a touch screen (or the screen 14 may be made responsive to tactile input) or any other controls operable by the operator of the system 2. In one exemplary embodiment, a disposable overlay (not shown) may be applied over the user interface 12. For example, if the display screen 14 is a touch screen and the operator intermittently provides input to the user interface 12 by touching the display screen 14, an overlay may be used to prevent the display screen 14 from becoming damaged or obscured by fluid.

The housing 10 may further include a handle 18 for steering the system 5 and a slot 26 receiving a cassette 28, which is described below. In the exemplary embodiment, the handle 18 includes an alignment beam activator 20 which, when pressed, causes a light beam (e.g., laser light) to be emitted from a beam exit port 24 on the console 4. As would be understood by those skilled in the art, the light beam may preferably be oriented horizontally so that, as the height of the console 4 is adjusted using the height adjusting mechanism on the stand 8 until the beam is positioned on a desired portion of the patient's anatomy, the operator will know that the console 4 is in a desired position relative to the uterus. Making the console 4 a desired height off the floor relative to the uterus (e.g., the same height) ensures that a pressure with which the fluid is circulated in the uterus does not exceed a predetermined value. Those of skill in the art will understand that the activator 20 may be disposed adjacent to the user interface 12 and/or the keypad 16 may be positioned on the handle 18. The housing 10 preferably also includes a hook 22 for hanging a drainage bag (not shown) from the console 4. After ablating the endometrial lining, the fluid is discharged into the drainage bag.

Figure 3:
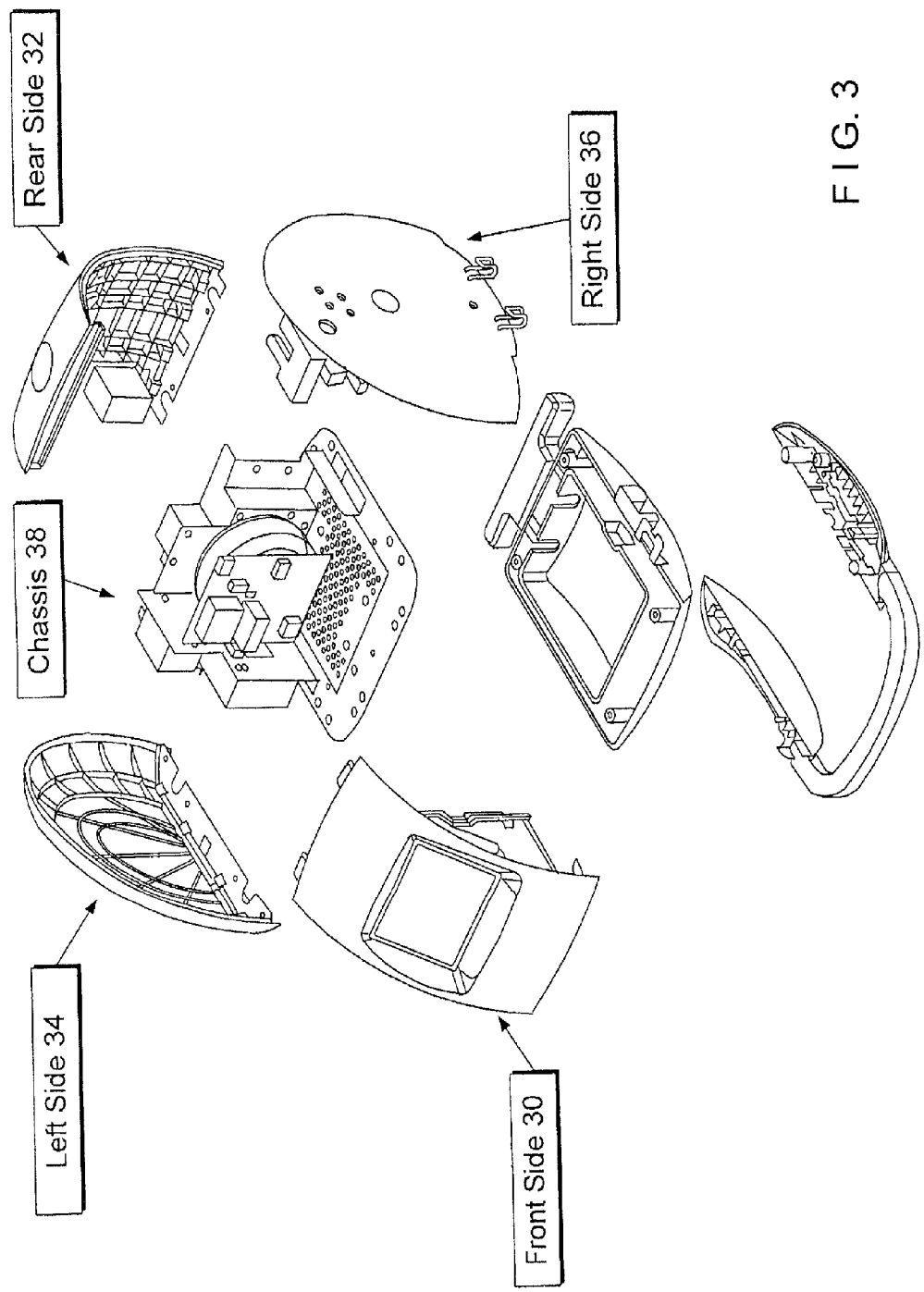
FIG. 3 shows an exploded view of an exemplary embodiment of a console of a thermal ablation system according to the present invention.

FIG. 3 shows internal components of an exemplary console 4 according to the present invention. The housing 10 of the console 4 includes a front side 30, a rear side 32, a left side 34 and a right side 36. Those of skill in the art will understand that the housing 10 may be comprised of any number of components in any number of geometrical relationships to one another and that the terms front, rear, left and right are relational terms used only to describe the exemplary embodiment of the console 4. A chassis 38 inside the housing 10 acts as an attachment point for the sides 30, 32, 34, 36 and supports various electrical components of the console 4. In this embodiment, the front side 30 includes circuitry powering the user interface 12 and the beam activator 20, while the rear side 32 provides an input for a power source (e.g., line voltage). However, in other exemplary embodiments, the system 2 may be powered by an on-board battery. The left side 34 generally comprises a vented wall which allows air heated during operation of the electric components of the console 4 to be expelled therefrom, while the right side 36 includes components that interface with the cassette 28.

Figure 4:
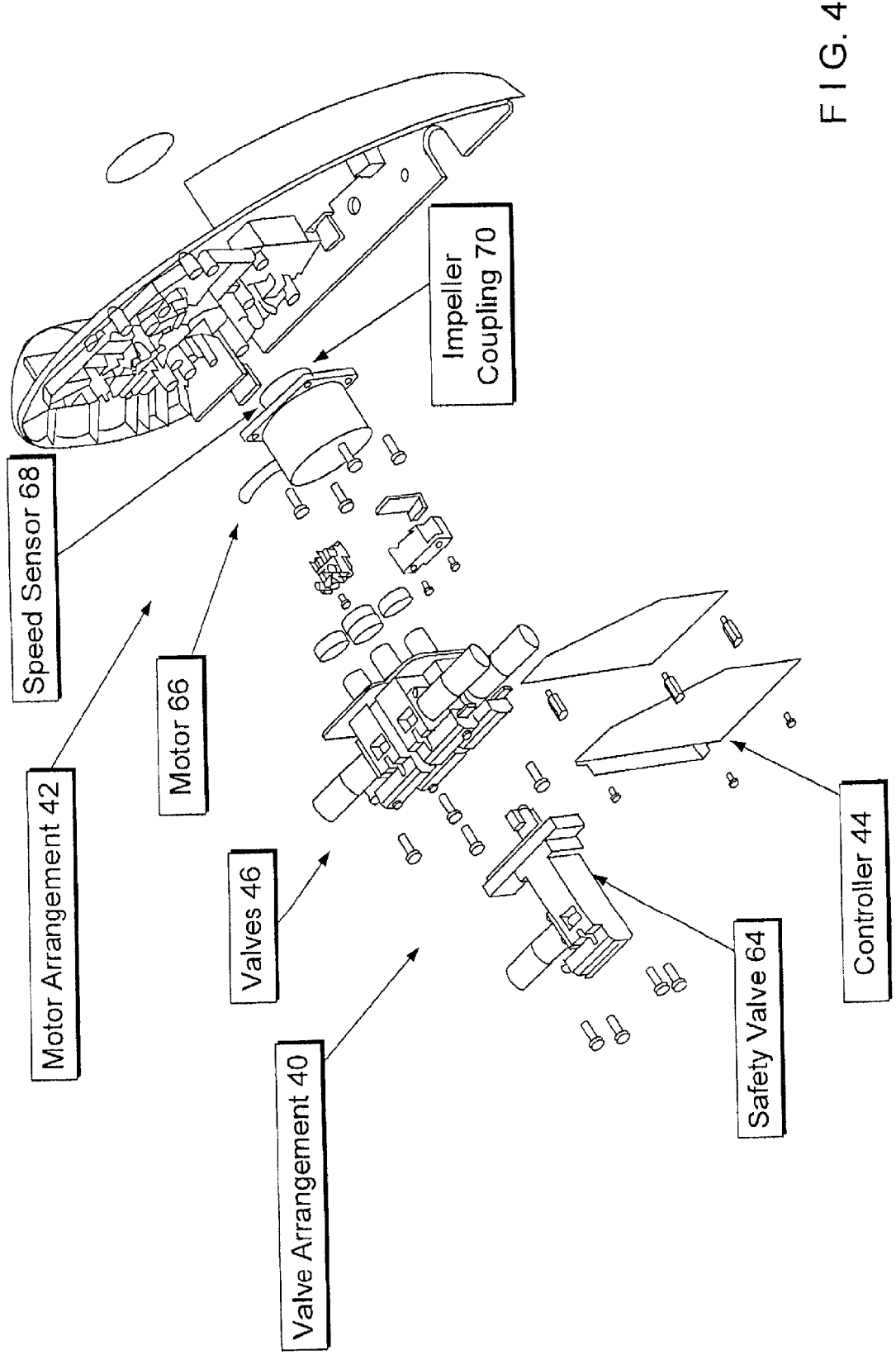
FIG. 4 shows an exploded view of an exemplary embodiment of a right side component of a console of a thermal ablation system according to the present invention.
Figure 5:
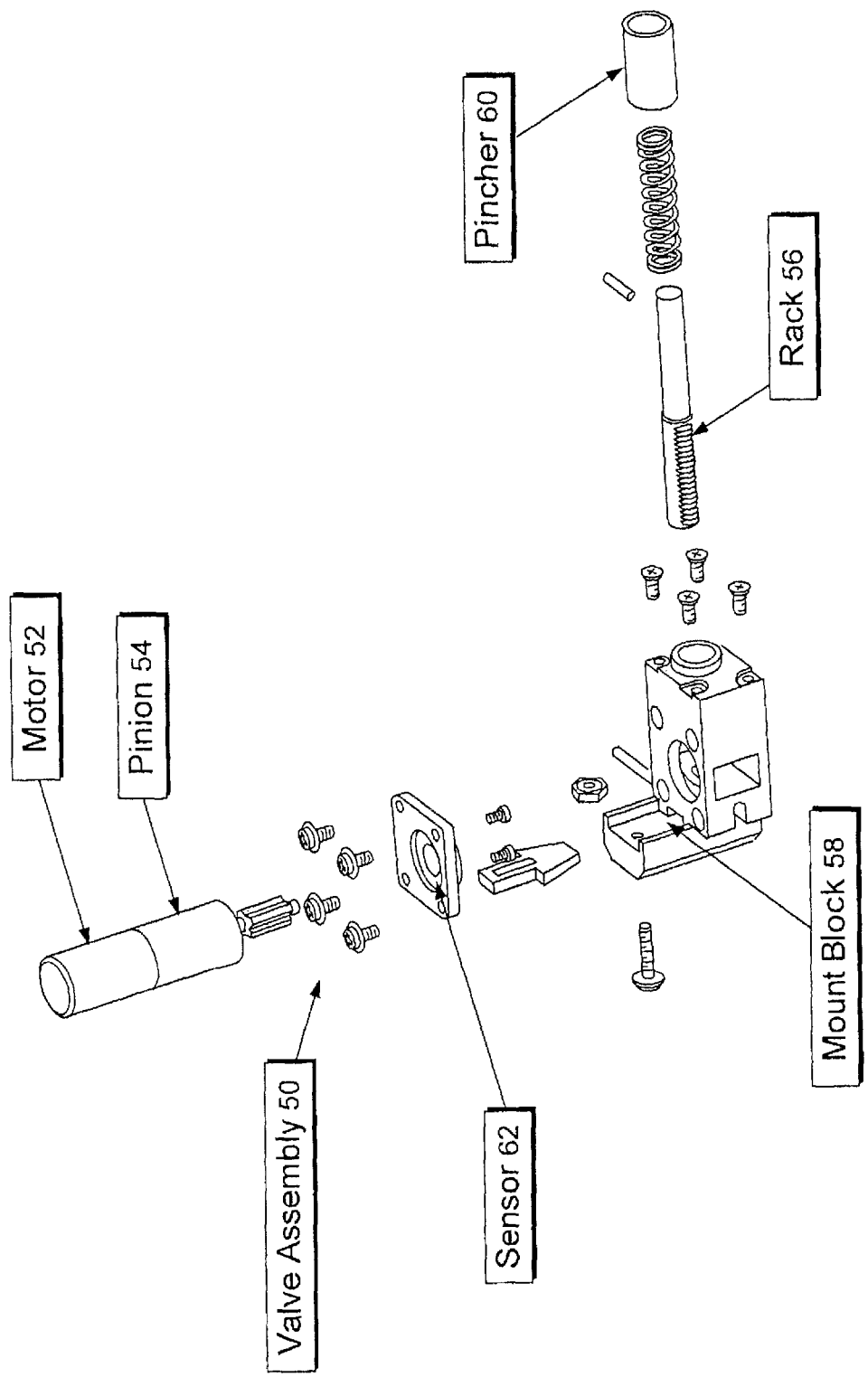
FIG. 5 shows an exploded view of an exemplary embodiment of a valve assembly for a console of a thermal ablation system according to the present invention.

FIG. 4 shows an exemplary embodiment of the right side 36 of the console 4 which includes components for interfacing with the cassette 28. The cassette interface generally includes a valve arrangement 40 and a motor arrangement 42. The valve arrangement 40 includes one or more valves 46 (e.g., pinch valves) which engage outer surfaces of flexible tubes within the cassette 28 via openings in a rigid housing thereof to selectively open and close the tubes without contacting fluids flowing therethrough. As shown in FIG. 5, an exemplary valve assembly 50 is a pinch valve. However, those of skill in the art will understand that the functions of the valves 46 may be performed by any device(s) configured to selectively open and close the tubes in the cassette 28 without contacting fluids within the tubes.

As shown in FIG. 5, the valve assembly 50 includes a motor 52 which drives rotation of a pinion 54 that mates with a rack 56. Rotation of the pinion 54 is translated into axial movement of the rack 56 in distal (lumen-closing) and proximal (lumen-opening) directions relative to a mount block 58 with a pincher 60 coupled to a distal end of the rack 56. As the rack 56 is driven distally by the rotation of the pinion 54, the pincher 60 compresses a respective lumen in the cassette 28 against a wall of the cassette 28. A position sensor 62 (e.g., an optical sensor, Hall effect sensor, etc.) may be included in the valve assembly 50 to determine a position of the pincher 60 relative to the respective lumen. In this manner, an amount of closure of the respective lumen and/or an amount of fluid flow permitted through the respective lumen at the amount of closure may be determined. As will be described further below, the system 2 may utilize the closure information to adjust a volume and/or pressure of fluid circulated through the uterus.

Referring back to FIG. 4, the valves 46 may include a number of valve assemblies 50 including similar rack and pinion assemblies and pincher combinations or other mechanisms corresponding to a number of lumens in the cassette 28 to be selectively opened and closed. The valve arrangement 40 may further include a safety valve 64 which closes whenever a pressure within the lumen exceeds a predetermined maximum pressure or whenever an unsafe condition is detected.

The motor arrangement 42 includes a motor 66 (e.g., a DC brushless motor), a speed sensor 68 and an impeller coupling 70. Current supplied to the motor 66 rotates an armature thereof which, in turn, rotates the impeller coupling 70. In one exemplary embodiment, the impeller coupling 70 includes one or more magnets which, when the cassette 28 is inserted into the console 4, are magnetically coupled to one or more magnets on an impeller in the cassette 28 so that rotation of the impeller coupling 70 rotates the impeller to drive fluid through the cassette 28 and into the patient with no contact between fluid in the cassette 28 and components of the console 4 outside the cassette 28. Those of skill in the art will understand that the impeller coupling 70 and the impeller are an exemplary embodiment of any pump arrangement which may be used to output fluid from the cassette 28. The speed sensor 68 may be coupled to the motor 66 to detect a rotational speed of the armature thereof to determine, for example, a speed (and/or pressure) at which fluid is being circulated through the cassette 28 and/or the uterus.

Figure 6:
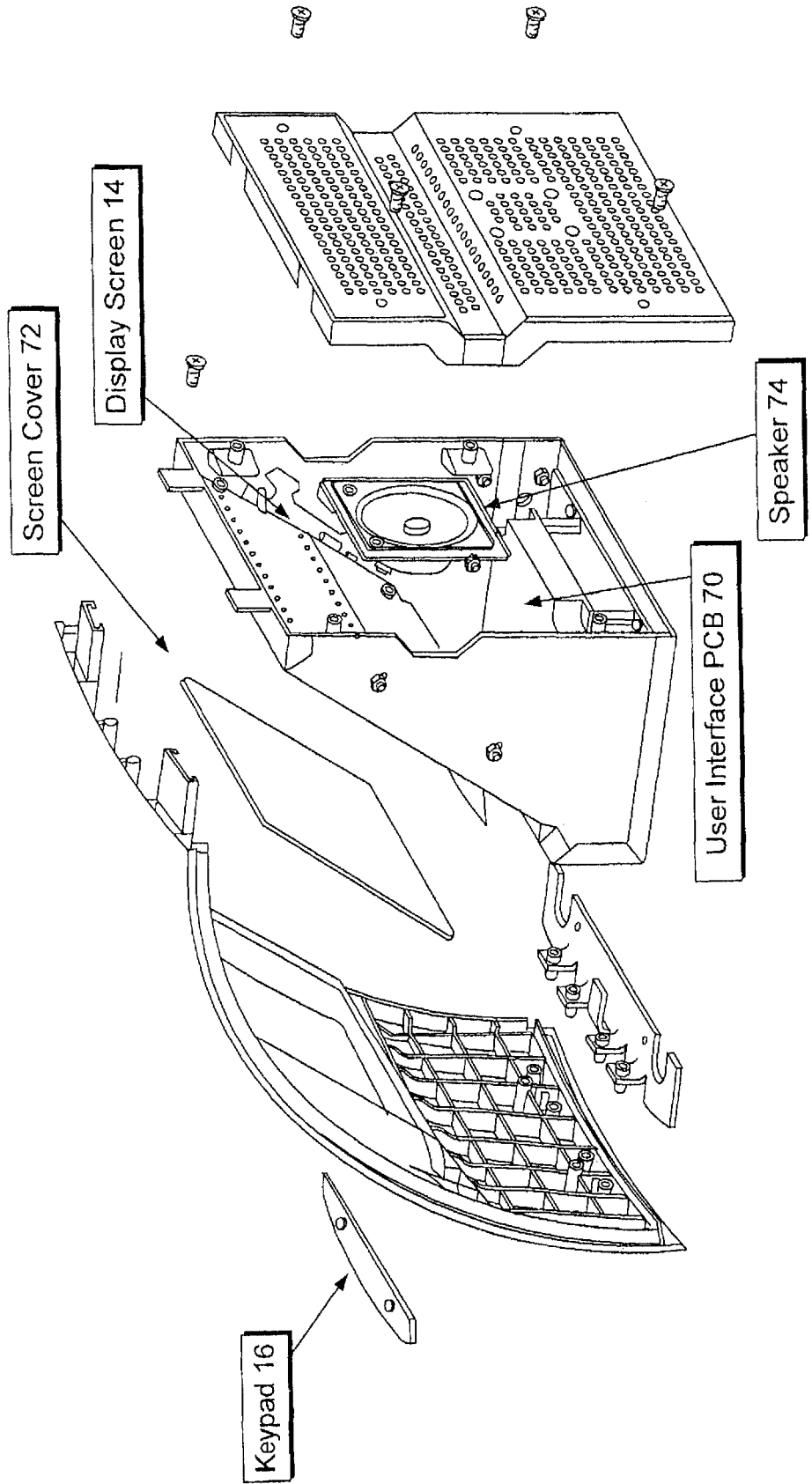
FIG. 6 shows an exploded view of an exemplary embodiment of a front side component of a console of a thermal ablation system according to the present invention.

As shown in FIG. 6, an exemplary embodiment of the front side 30 of the console 4 includes the user interface 12, the display screen 14 and the keypad 16 which may be controlled by a user interface printed circuit board (PCB) 70 which interprets user input entered via the keypad 16 and displays the content on the display screen 14. A screen cover 72 may be overlaid on the display screen 14 to protect and allow cleansing thereof. The disposable overlay described above is preferably overlaid on the screen cover 72. A speaker 74 disposed within the console 4 may be utilized to provide to the operator audible signals such as, for example, voice instructions, warning signals, etc. which, when used in conjunction with the visual content presented on the display screen 14 facilitate operation of the system 2. Additionally, the audible output may be useful when, for example, two persons are working in conjunction to perform the ablation procedure. That is, the operator may be monitoring operation of the system 2, while a physician and/or nurse may be monitoring the fluid circulation through the uterus. The audible output makes both persons aware of the progress of the ablation procedure regardless their fields of view.

Figure 7:
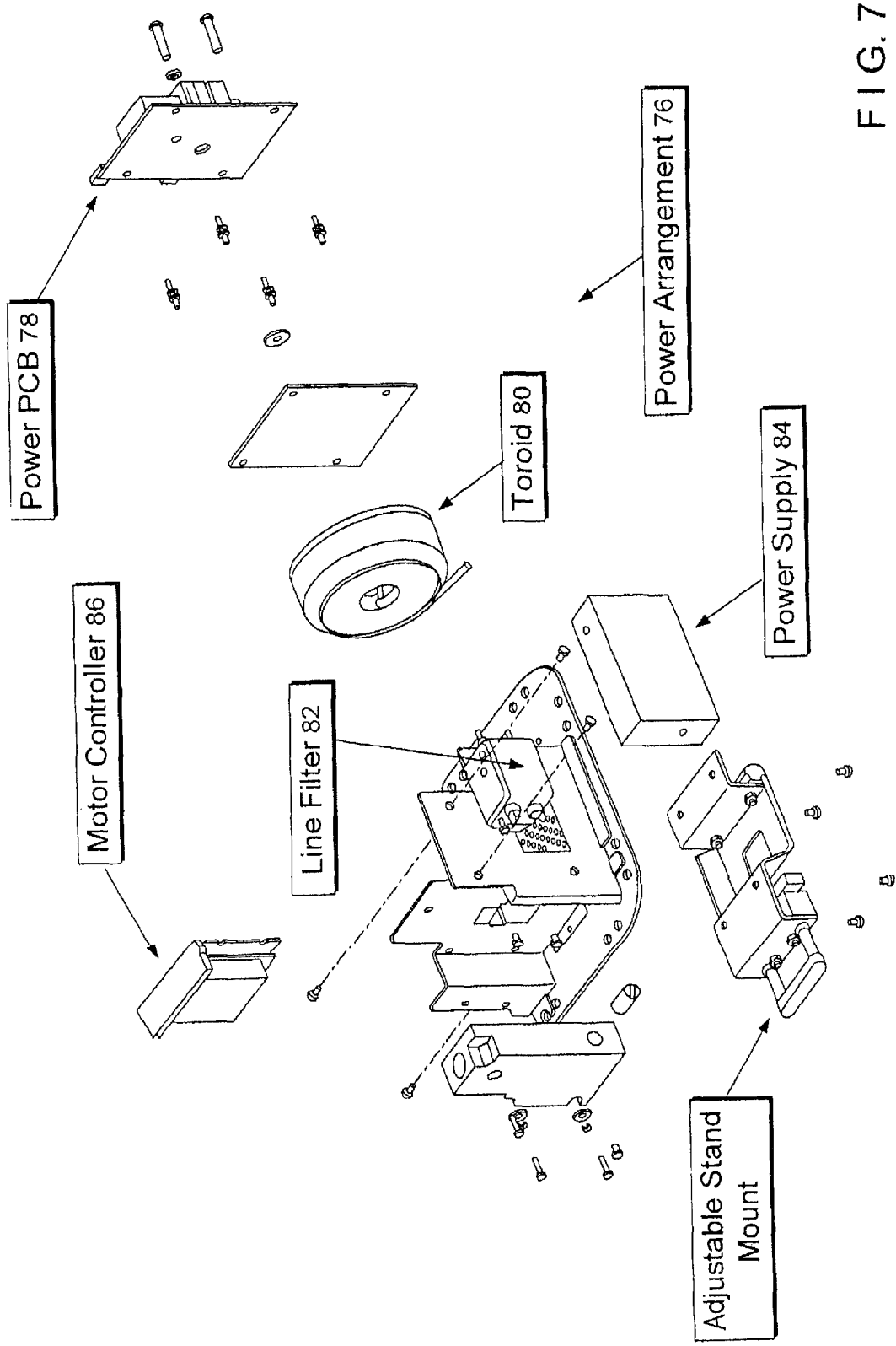
FIG. 7 shows an exploded view of an exemplary embodiment of a chassis of a console of a thermal ablation system according to the present invention.

As shown in FIG. 7, the chassis 38 in the console 4 according to the exemplary embodiment is encased by the right, left, front and rear sides 30, 32, 34, 36 of the housing 10. A power arrangement 76 mounted on the chassis 38 includes a power PCB 78, a toroid 80, a line filter 82 and a power supply 84 coupled to, for example, a port for receiving a line voltage. For example, the power supply 84 may have a power cord extending therefrom to be plugged into a wall outlet, or the port may receive a plug as part of an extension cord. The line filter 82 treats the power to, for example, eliminate surges, harmonic transient currents, spikes, etc, in the current being delivered to the console 4. The filtered current is then transmitted to the power PCB 78 which distributes power to operational components of the system 2. The toroid 80 operates as a transformer, providing electrical isolation between circuits in the console 4.

Also mounted on the chassis 38 is a motor controller 86 which receives instructions from a controller 44 to control operation of the motor 66. The controller 44, which is shown in FIG. 4, may be a central processing unit which coordinates operation of the system 2 during the ablation procedure. That is, the controller 44 may process an instruction set stored in a memory for controlling the user interface 12, the motor 66, the valves 46, the safety valve 64, etc. during the ablation procedure. An exemplary use of the system 2 for performing an ablation procedure will be explained in more detail below.

Figure 8:
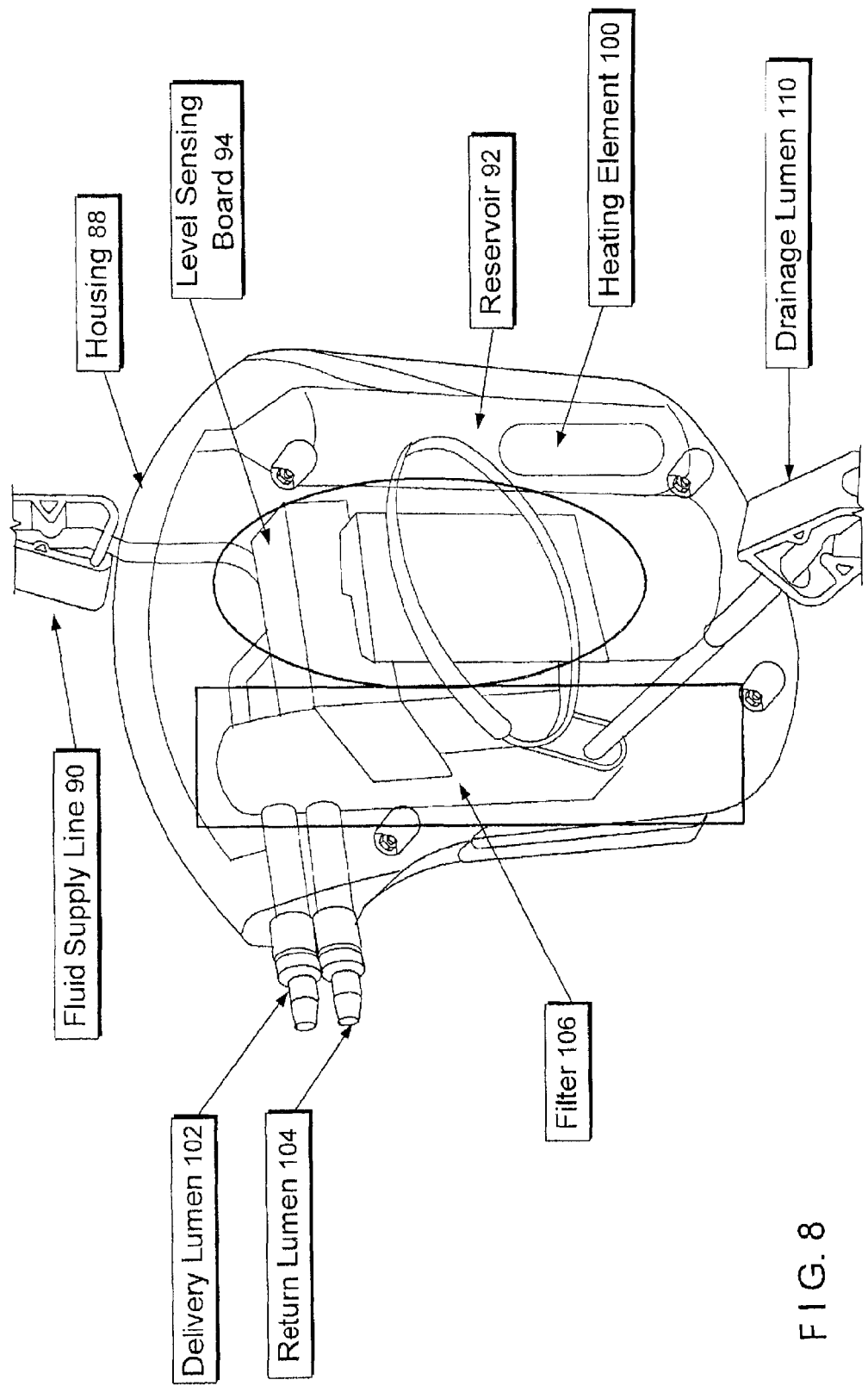
FIG. 8 shows an outer view of an exemplary embodiment of a cassette of a thermal ablation system according to the present invention.
Figure 9:
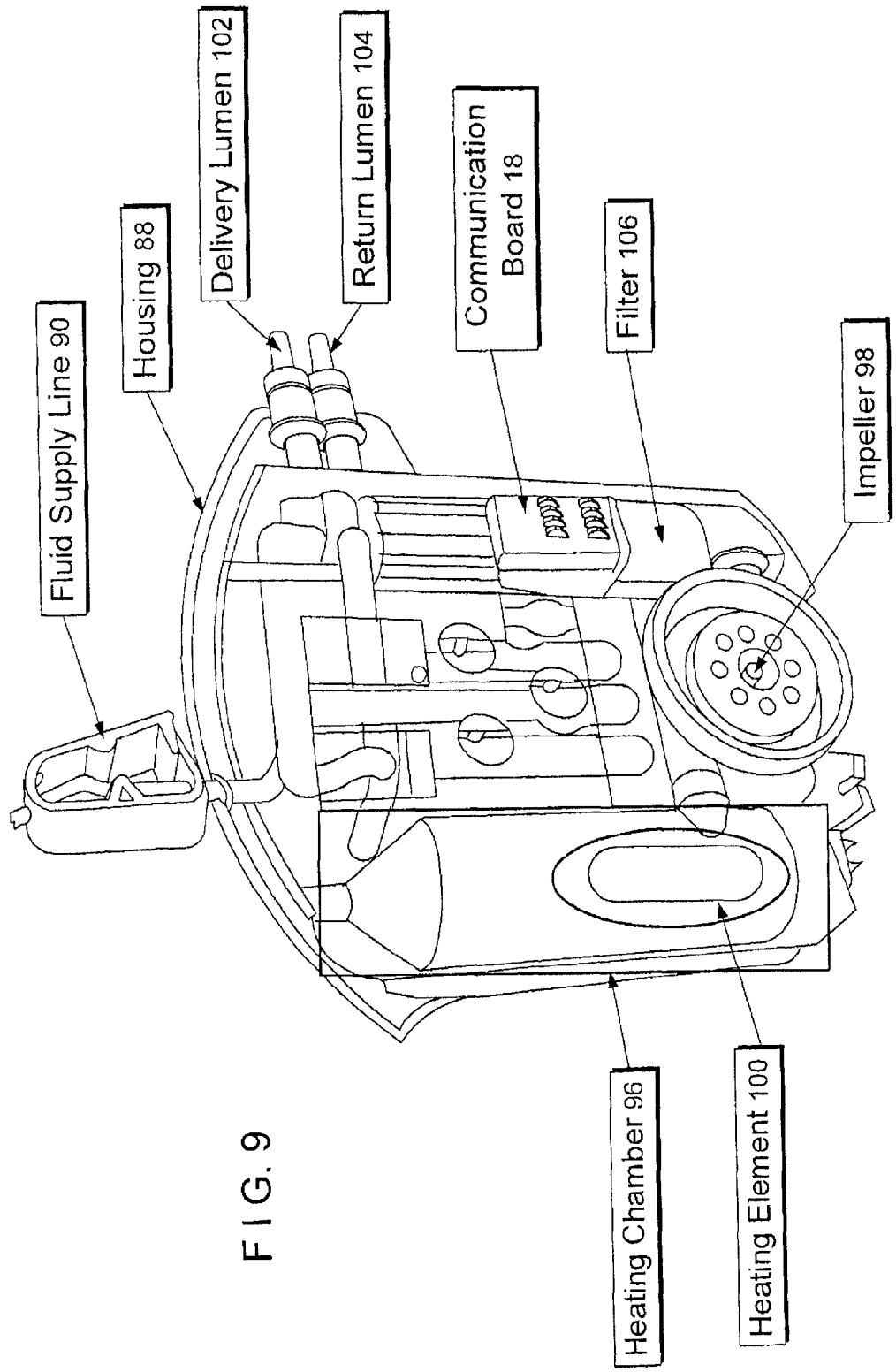
FIG. 9 shows an inner view of an exemplary embodiment of a cassette of a thermal ablation system according to the present invention.

FIGS. 8 and 9 show an exemplary embodiment of the cassette 28 according to the present invention. As noted above, the cassette 28 may be embodied in a housing 88 sized and shaped to fit within the slot 26 on the console 4. For example, the housing 88 may include rails along its sidewalls which are received by guides on the sidewalls of the slot 26, allowing the cassette 28 to slide thereinto. Once in the slot 26, the cassette 28 may be mechanically locked in place (e.g., latches, hooks, etc.), gravitationally held in the slot 26, magnetically coupled to the console 4, etc. In one exemplary embodiment, the instructions provided on the user interface 12 may instruct the operator on how and when to insert and remove the cassette 28. The console 4 may lock the cassette 28 in the slot 26 to prevent removal during an ablation procedure.

The fluid from the IV bag enters the cassette 28 via a fluid supply lumen 90 which terminates in a reservoir 92. In this embodiment, a level sensing board 94 is disposed within the reservoir 92 for monitoring a volume of fluid therein. During the ablation procedure, the controller 44 compares the volume to a predetermined volume (or range thereof) to determine whether fluid has been lost/leaked. Based on the results of the comparison, the system 2 may shut down or execute a predetermined safety procedure. In the exemplary embodiment, the level sensing board 94 comprises a plurality of level sensors (e.g., capacitors) arranged along a height of the board 94. By analyzing signals received from the level sensors, the controller 44 may determine the volume of the fluid within the reservoir 92.

The safety procedure may be one or more sets of instructions stored in one or more locations to create a redundant, safety net. For example, a primary safety system may be stored as a set of instructions for execution by the controller 44 so that, when the controller 44 is alerted to any of a number of predefined faults, the controller initiates the safety procedure and puts the system into a safe state. In addition, a secondary safety system may be included in the form, for example, of a separate non-volatile memory of a complex programmable logic device (CPLD) coupled to the controller 44 to monitor a watchdog signal therefrom. If a problem arises which compromises the integrity of the controller 44, the watchdog signal will be compromised as well and the CPLD will put the system into the safe state. The safety procedure may be executed if, for example, the controller 44 indicates that a component of the system 2 is non-responsive or otherwise malfunctioning while the secondary system (i.e., the CPLD) will put the system in the safe state when the controller 44 malfunctions.

The fluid in the reservoir 92 is directed into a heating chamber 96 by an impeller 98 which, as described above, is rotated by the impeller coupling 70 in the console 4. As shown in FIGS. 14 and 15, an exemplary embodiment of the impeller 98 includes a plurality of veins 160 disposed on a first surface and a plurality of magnets 162 disposed on a second surface. Each of the veins 160 may be formed as a concave projection on the first surface and have a predefined spacing and angle relative to adjacent veins. In this configuration, the fluid interfacing with the impeller 98 is forced from a center of rotation thereof and into the heating chamber 96. The magnets 162 may be embedded in the impeller 98 having exposed surfaces flush with the second surface which magnetically couple to the magnets on the impeller coupling 70. An interface between the impeller 98 and the impeller coupling 70 may be configured so that only the first surface of the impeller 98 comes into contact with the fluid, while the second surface is exposed on (and/or forms a part of) an external surface of the cassette 28. Alternatively, the impeller 98 may be fully enclosed within the cassette 28.

The heating chamber 96 includes a heating element 100 which heats the fluid therein. Operation of the heating element 100 may be based on a temperature measurement of the fluid obtained by a temperature sensor (e.g., thermistor) in the heating chamber 96. By monitoring the temperature measurement, the controller 44 ensures that the fluid temperature is within a predetermined range (e.g., a temperature hot enough to ablate tissue). Those of skill in the art will understand that the heating element 100 may further include a cooling element or be deactivated when, for example, the ablation procedure has been completed and the remaining surface tissue in the uterus is to be allowed to cool.

Figure 13:
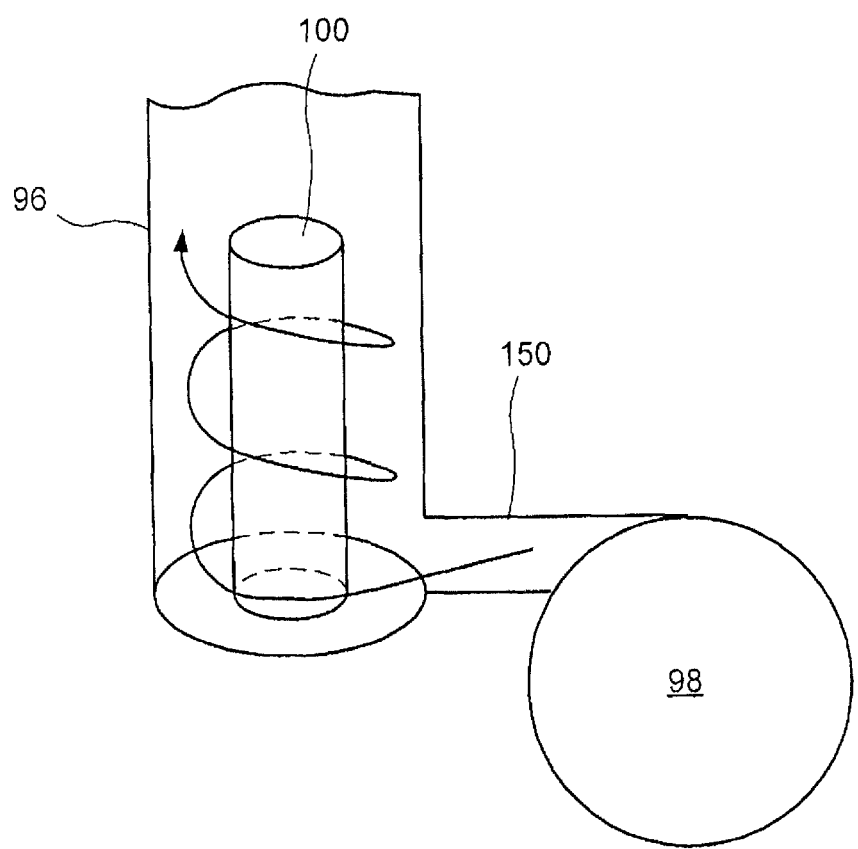
FIG. 13 shows an exemplary embodiment of fluid flow through a heating chamber in a cassette according to the present invention.

As shown in FIG. 13, the heating chamber 96, in this embodiment, is substantially cylindrical with a fluid inlet 150 at a lower end thereof. The inlet 150, which receives fluid pumped from the impeller 98, is directed substantially tangential to the cylinder so that the fluid swirls around the heating chamber 96 and is heated by the heating element 100 as it rises to an outlet at the top of the cylinder. The heating element 100 extends substantially along a longitudinal axis of the cylinder so that the fluid travels around the heating element 100 in a substantially helical path as it rises in the heating chamber 96, maximizing energy transfer to the fluid.

When the fluid exits the heating chamber 96 it has reached the desired temperature leaving the cassette 28 via a delivery lumen 102 to pass to an introducer which has been inserted into the uterus. The fluid is then circulated through the uterus and returned to the cassette 28 via a return lumen 104. The returned fluid is then passed through a filter 106 to remove any tissue remnants, coagulated plasma, etc. and fed back through the impeller 98 into the heating chamber 96. By continuously circulating the returned fluid while monitoring any volumes of fluid added/removed from the system 2, the controller 44 can detect changes from the initial fluid volume as described above to determine a volume of fluid absorbed into the body. When the ablation procedure has been completed, the fluid is drained into the drainage bag via a drainage lumen 110.

Electrical signals generated by the temperature sensors in the heating chamber 96 and the level sensors in the reservoir 12 are transferred to the controller 44 via a communications circuit board 108 and digitized. The digitized signals are then converted into procedural data (e.g., temperature data and volume data) which is analyzed by the controller 44 to monitor the progress of the ablation procedure.

Figure 11:
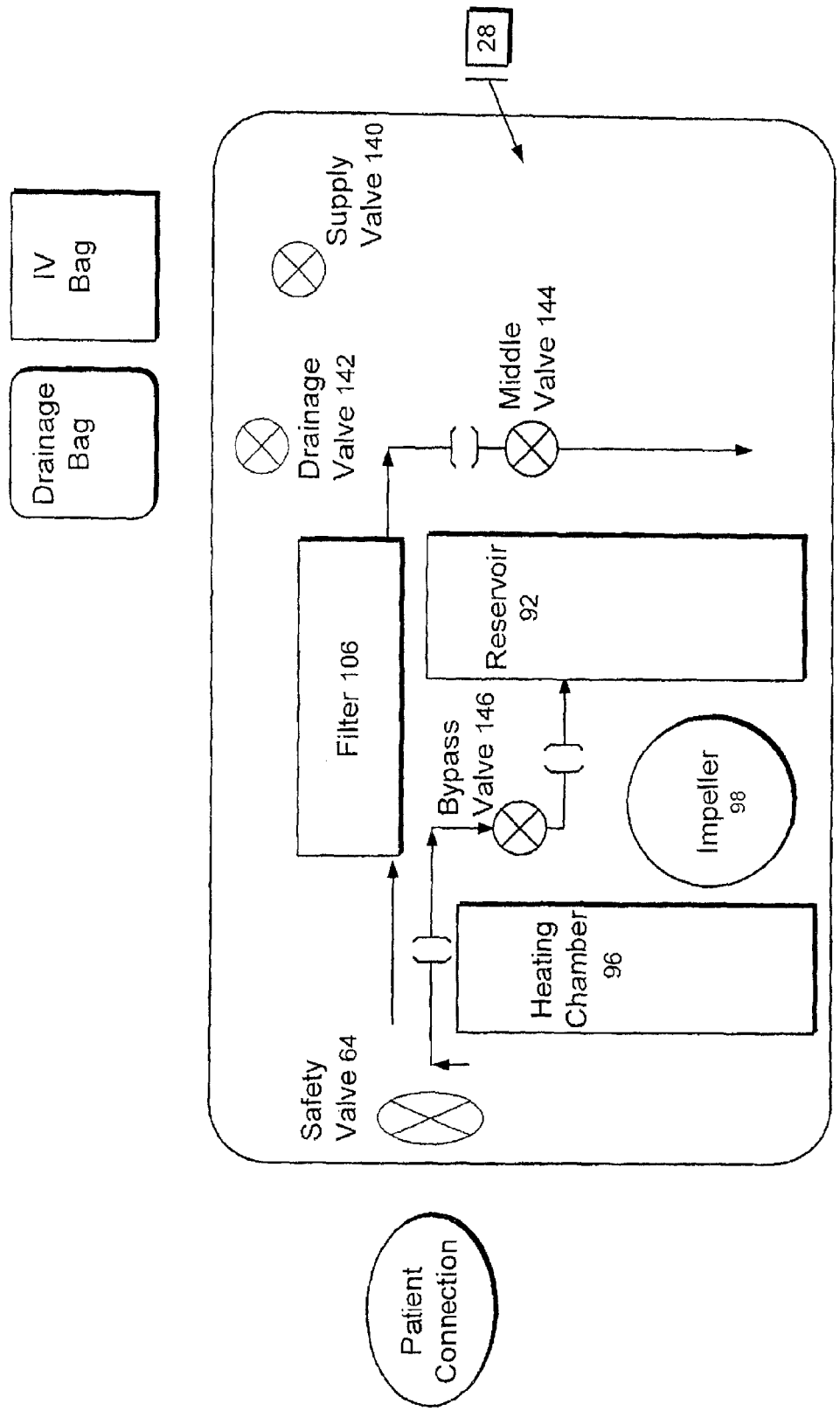
FIG. 11 shows an exemplary embodiment of an open loop fluid flow path of a thermal ablation system according to the present invention.
Figure 12:
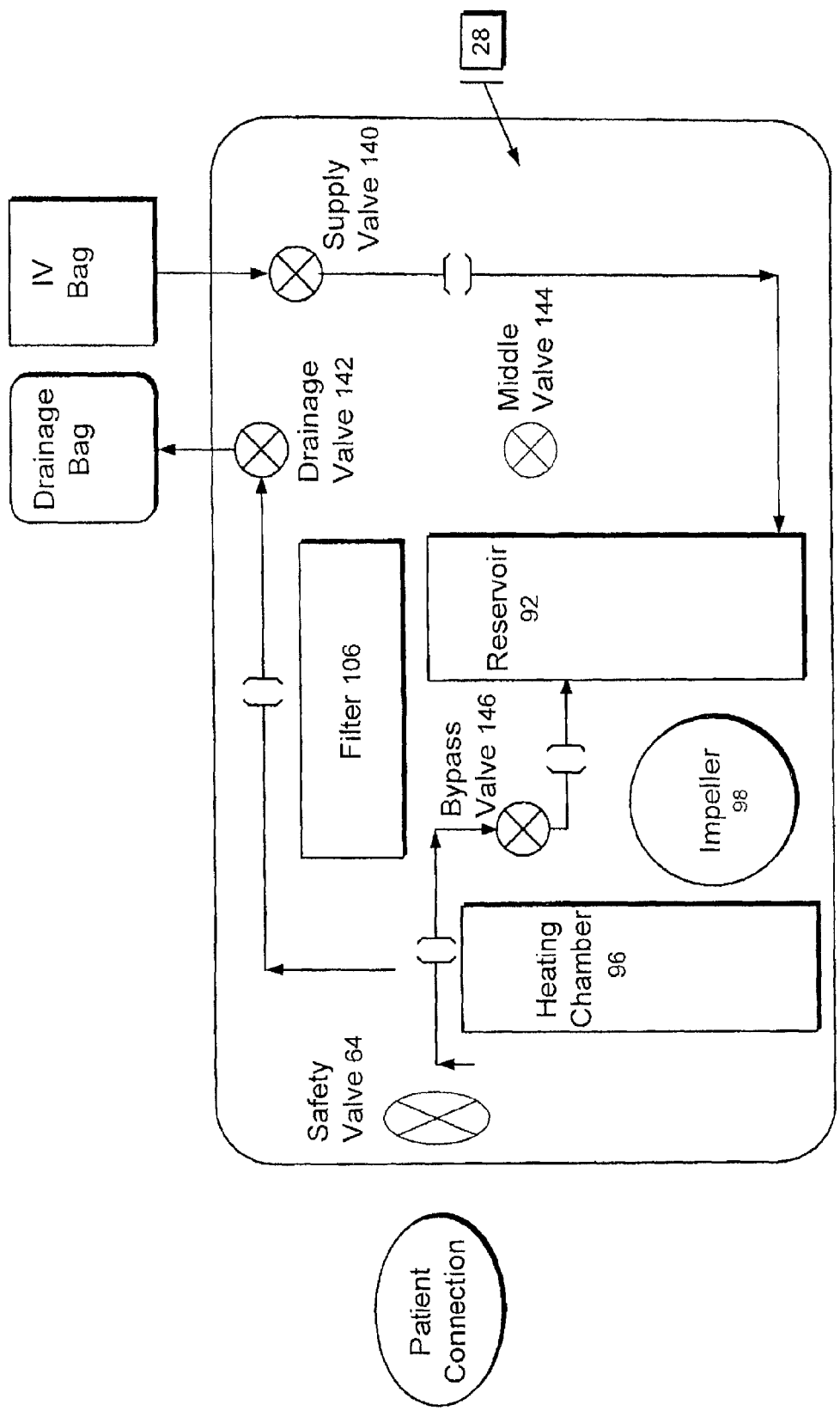
FIG. 12 shows an exemplary embodiment of a closed loop fluid flow path of a thermal ablation system according to the present invention.

During progression of the ablation procedure, the controller 44 configures alternative fluid flow paths through the cassette 28 by selectively controlling operation of the valves 46 to open and close the fluid flow lumens therein. FIG. 11 shows an open loop flow path used during priming and/or cooling stages of the ablation procedure. For example, the system primes by opening the supply valve 140 to permit fluid from the IV bag through the cassette 28 to the reservoir 92 and through the impeller 98 to the heating chamber 96 which is inactive at this point through the safety valve 64 into a delivery (not shown) of an introducer 112. The fluid exits the delivery lumen into the uterus and is drawn back from the uterus into a return lumen (not shown) of the introducer 112 which passes the fluid back through the safety valve 64 and out to a drainage bag via a drainage valve 142. When the system has been primed, the valves of the cassette 28 are reconfigured to the closed loop configuration of FIG. 12 for heating of the fluid and ablation. Specifically, the drainage valve 142 is closed so that fluid circulates from the reservoir 92, through the impeller 98 and the heating chamber 96 and into the uterus via the safety valve 64 and the introducer 112. The fluid returning from the uterus via the return lumen 104 of the introducer 112 passes through the safety valve 64 and the filter 106 to return to the reservoir 92 via the middle valve 144 and continues to circulate through this path during the ablation procedure. In this configuration, the heating chamber 96 is active to raise the temperature of the fluid to a desired level for ablation. In addition, in this configuration, the bypass valve 146 is opened when necessary to bleed off excess flow from the output from the heating chamber 96 returning this bled-off fluid to the reservoir 92 without passing through the uterus. When the procedure has been completed, the drainage valve 142 is opened and the bypass valve 146 and the middle valve 144 are closed to return the system 100 to the open-loop configuration of FIG. 11. The heating chamber 96 is deactivated at this point so that fluid currently circulating in the cassette 28 flows through the uterus and passes through the drainage valve 142 to the drainage bag without further heating. After this fluid has been drained, fresh fluid from the IV bag is passed through the cassette 28 into the uterus at substantially room temperature to flow out into the drainage bag until a desired amount of cooling has been achieved.

Figure 10:
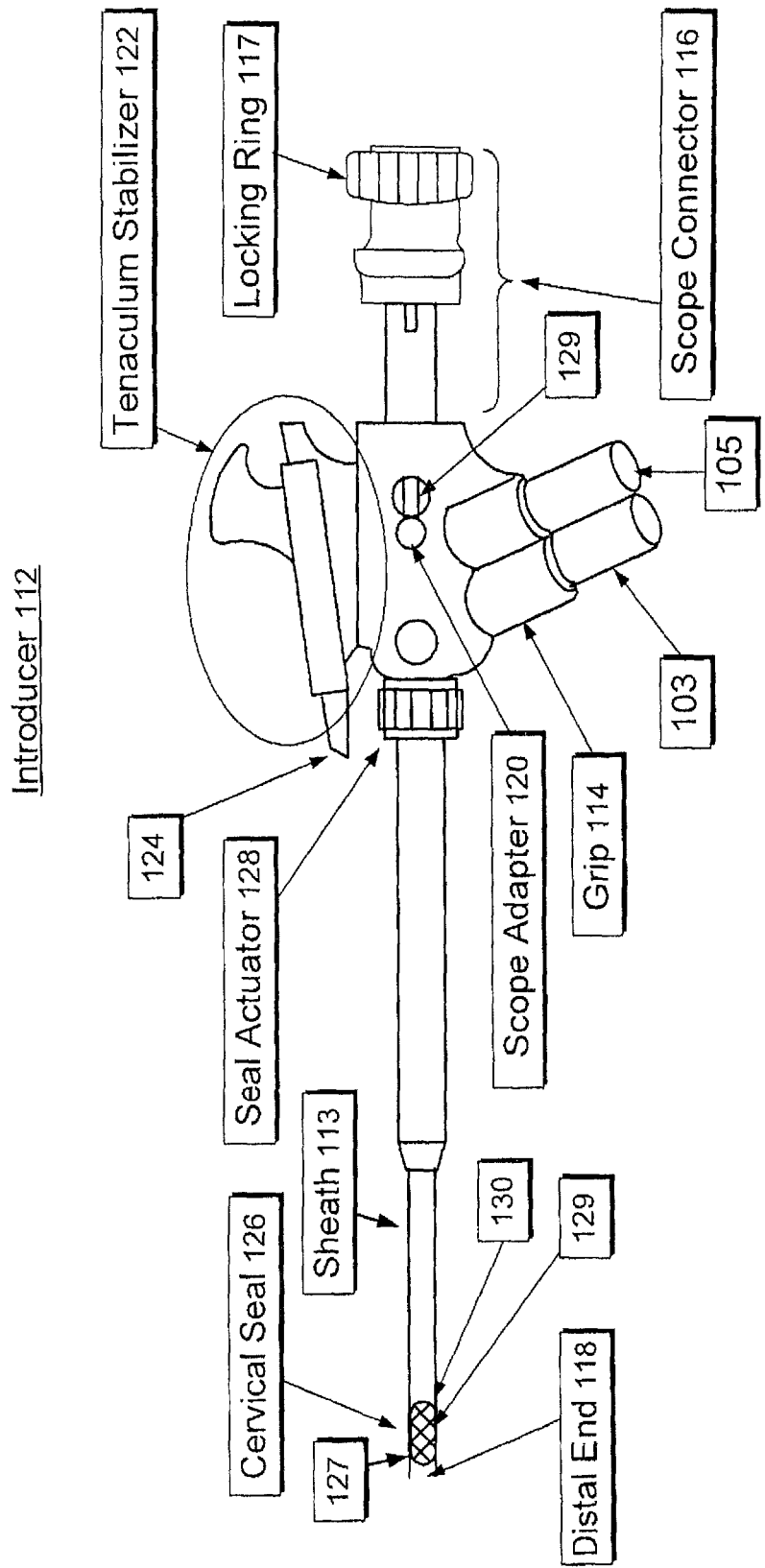
FIG. 10 shows an exemplary embodiment of an introducer of a thermal ablation system according to the present invention.

As shown in FIG. 10, an introducer 112 according to an exemplary embodiment of the present invention is coupled to the cassette 28 via tubes 103 and 105 to deliver fluid to the uterus and to return the fluid from the uterus to the cassette 28. The tubes 103, 105 are coupled to delivery and return lumens 102, 104, respectively, of the cassette 28 and to fluid delivery and return lumens (not shown) within a sheath 113 of the introducer 112. The fluid delivery and return lumens of the introducer 112 terminate at respective openings at a distal end 118 of the sheath 113 which, when the introducer 112 is in an operative positions, is located within the uterus. The introducer 112 may optionally include a vision system to allow visualization of the operative area. Those of skill in the art will understand that the vision system may be substantially similar to the systems in conventional endoscopes (e.g., fiber optic or CCD-based systems). Alternatively, users may rely on the vision system of an endoscope or other instrument inserted through the introducer 112, as described below.

The introducer 112 includes a grip 114 (e.g., an ergonomic handle) coupled to the sheath 113 and a scope connector 116 for receiving a visualization device, such as an endoscope. The grip 114 facilitates holding and manipulation of the introducer 112 with a single hand while the operator uses his free hand to interface with the console 4, adjust the visualization device, manipulate the patient's anatomy, etc. The scope connector 116 according to this embodiment is disposed on a proximal end of the introducer 112 and provides an attachment point for the visualization device (e.g., a hysteroscope, an endoscope) so that the visualization device may be passed distally through a visualization lumen in the introducer 112 and extended out of the distal end 118. Thus, the operator may visually monitor insertion of the introducer 112 into the uterus.

The scope connector 116 may comprise an optional locking ring 117 and a scope adapter 120 which allow the introducer 112 to be adjusted to accommodate visualization devices of varying lengths. The visualization device is inserted into the proximal end of the introducer 112 through the scope connector 116 and locked thereto using the locking ring 117. The user then depresses the scope adapter 120 releasing the scope adapter 120 from a current locking aperture 121. This allows the scope connector 116 to slide proximally out of or distally into the introducer 112 so that, when the visualization device has been inserted through the sheath 113 to a desired position in the uterus, the scope connector 116 supports the portion of the visualization device extending out of the introducer (e.g., a proximal end of an endoscope immediately distal of the control handle). Those of skill in the art will understand that the scope connector 116 may be implemented as any mechanism which allows the length of the introducer 112 to be adjusted to and maintained at a new length. For example, as shown in FIG. 10, the scope adapter 120 is formed as a projection on an outer surface of a distal portion of the scope connector 116 received in and movable between one of a number of locking apertures 121 formed on the grip 114. Partial barriers may be formed between each of the locking apertures 121 to retain the scope adapter 120 in a selected one of the locking apertures 121 maintaining a selected length of a portion of the scope connector 116 projecting from the proximal end of the introducer 112. In another embodiment, a rack may be formed on the distal portion of the scope connector 116 mating with a gear in the grip 114 so that rotation of the gear extends and withdraws the scope connector 116 relative to the grip 114. A ratchet may be provided to maintain the gear in a fixed position relative to the rack, thereby maintaining the desired position of the scope connector 116 relative to the grip 114.

The grip 114 may further include an optional tenaculum stabilizer 122. For example, during the ablation procedure, a tenaculum may be employed around the cervix to enhance the seal of the cervix around the sheath 113 of the introducer 112. A tenaculum that has been clamped around the cervix may then be coupled to the introducer 112 to ensure that the introducer 112 remains at a desired position within the uterus and is not inadvertently withdrawn therefrom. That is, it is important to make sure that the distal end of the sheath 113 is not withdrawn proximally from the uterus during the procedure or non-targeted tissue will be exposed to the ablation fluid. Thus, a portion of the tenaculum is passed over the tenaculum stabilizer 122 preventing movement of the sheath 113 proximally relative to the tenaculum. That is, once a tenaculum has been locked in position on tissue, the tenaculum can be slipped over the tenaculum stabilizer 122. The tenaculum stabilizer 122 is moved to a proximal-most position permitted by the tenaculum. Specifically, in the exemplary embodiment, the tenaculum stabilizer 122 includes a fin slidably mounted on a rail 124 formed on the grip 114. The fin includes a hook which may receive finger grips or a crossbar of a tenaculum as would be understood by those skilled in the art. When the tenaculum is coupled to the tenaculum stabilizer 122, the operator selects a tension to be applied between the tenaculum and the introducer 112 by moving the fin along the rail 124. A positioning mechanism (e.g., ratchet, latch, clip, etc.) may be used to maintain a position of the fin relative to the rail 124, as would be understood by those skilled in the art. Such a tenaculum stabilizer device is described in a U.S. Patent Application Ser. No. 60/971,409, entitled TENACULUM STABILIZER DEVICE, naming as inventors Christopher L. Askin, Brian MacLean, Stephen Keaney, Jozef Slanda and Jeffrey Zerfas filed Sep. 11, 2007. The entire disclosure of this application is hereby incorporated by reference herein.

The introducer 112 may further include an optional cervical seal 126 separated from a distal end of the sheath 113 by a distance selected to ensure that, when the distal end of the sheath 113 is in a desired position within the uterus, the seal 126 is located within the cervix proximal to the cervical os C. When the distal end 118 of the introducer 112 is introduced into the uterus, the elasticity of the cervix provides a substantially fluid-tight seal around the sheath 113. However, to minimize the risk of ablation fluid escaping through the cervix to damage non-targeted tissue, the fluid-tight seal may be enhanced/maintained using the cervical seal 126. In the exemplary embodiment, the cervical seal 126 is formed as a flexible membrane 127 which overlies a wire mesh 129, a proximal end of which abuts a distal end of an expander member 130. A distal end of the cervical seal 126 is fixed to the sheath 113 while a proximal end is slidable along the sheath 113.

A seal actuator 128 comprises a ring rotatably mounted on the sheath 113 and coupled to the expander member 130 which, in this embodiment, is formed as an oversheath telescopically mounted over the sheath 113. The ring may be coupled to the oversheath in such a manner that rotation of the ring moves the oversheath proximally and distally over the sheath 113. For example, an outer portion of the proximal end of the oversheath may be threaded to mate with threads on an inner portion of the ring of the seal actuator 128 so that, when the ring is rotated in a first direction, the expander member 130 slides distally along the sheath 113 pushing the proximal end of the mesh 129 distally causing the cervical seal 126 to expand radially away from the sheath 113.

Figure 16:
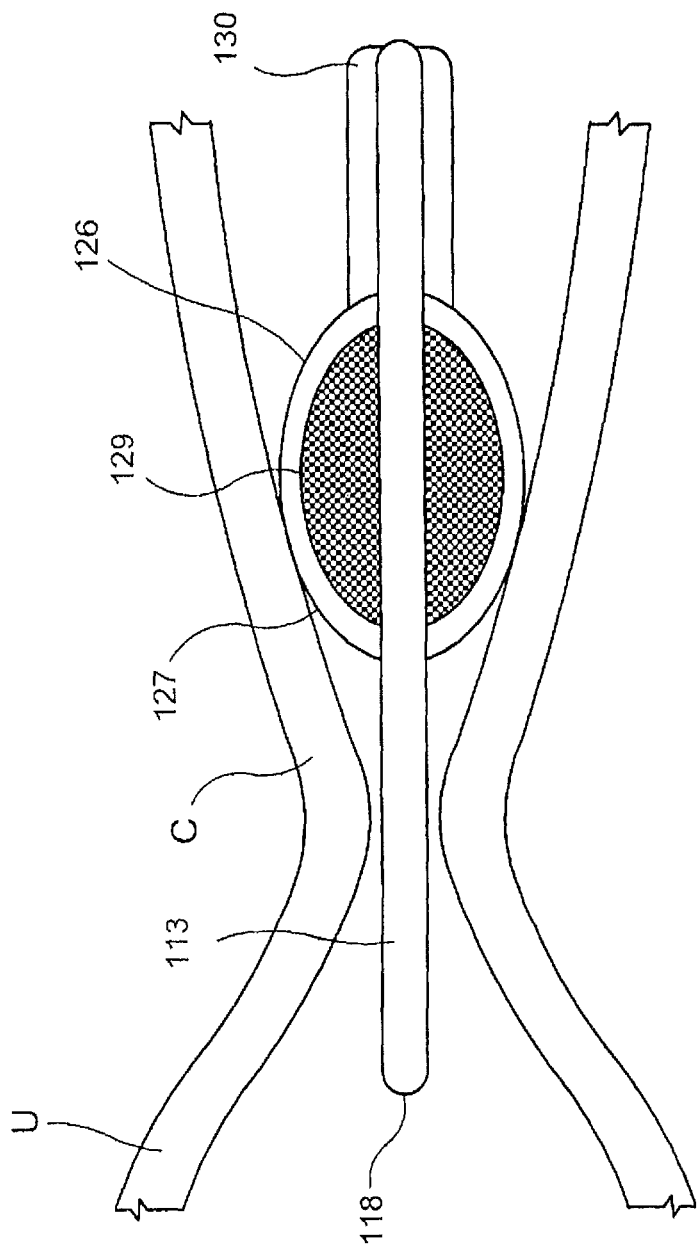
FIG. 16 shows an exemplary embodiment of a cervical seal of a thermal ablation system according to the present invention.

As shown in FIG. 16, it is preferable that expansion of the cervical seal 126 is executed when it is within the cervix proximal of the cervical os C so that none of the targeted tissue is covered by the seal 126. In the exemplary embodiment, the sheath 113 is moved distally until the distal end 118 thereof is within the uterus. The sheath 113 is then withdrawn proximally to minimize a projection of the sheath 113 into the uterus maximizing a field of view of the vision system. While in this position, the cervical seal 126 is positioned entirely within the cervix with a distal end of the seal 126 proximal of the cervical os C. The expander member 130 engages the proximal end of the cervical seal 126 and pushes the proximal end distally along the sheath 113 into the expanded position shown in FIG. 16. In the expanded position, the membrane 127 substantially engages an inner wall of the cervix enhancing the seal provided by the natural resilience of the wall of the cervix. The distance between the distal end 118 and the distal end of the cervical seal 126 is preferably between 0 and 1.5 cm which the seal is actuated. A seal 126 according to an exemplary embodiment of the invention may extend from a proximal end approximately 5 cm from the distal end 118 with a maximum diameter of the seal 126 corresponding to a distance of 1.5 cm from the distal end 118.

Rotation of the ring in a second direction withdraws the expander member 130, allowing the cervical seal 126 to return to its unexpanded state through the bias of the mesh 128 which tends toward the unexpanded state. Alternatively, the proximal end of the mesh 129 may be coupled to the distal end of the expander member 130 so that, as the expander member 130 is moved proximally, the mesh 129 is drawn back into the unexpanded state against a bias of the mesh 128 which tends to expand the seal 126.

In an exemplary use, the system 2 according to the present invention may be used to ablate the endometrial lining of the uterus. When the console 4 is activated, the display screen 14 may show (and the speaker 74 may provide) a pre-operative instruction set. For example, the instruction set may prompt the operator to hang the IV bag and the drainage bag. The controller 44 may then detect whether the cassette 28 has been inserted into the slot 26 and provide instructions regarding a procedure for connecting the cassette 28 to the IV bag, the drainage bag and the introducer 112. In addition, the controller 44 may determine, upon detecting the presence of the cassette 28, whether the cassette 28 has been previously used and prevent operation or take other pre-ordained steps if prior use is detected.

The pre-operative instruction set may also instruct the operator to adjust a height of the console 4 to be substantially equal with a height of the uterus or to achieve some other desired relationship between the height of the console 4 and that of the uterus. In the exemplary embodiment, the height of the console 4 is varied by adjusting the stand 8 using a light beam (e.g., laser) emitted from the beam exit port 24 to ensure that the console 4 is level with the uterus. When the console 4 is level with the uterus, the operator may initiate the ablation procedure by inserting the introducer 112 into the uterus via the cervix and expanding the cervical seal 126 within the cervix. The controller 44 may then configure the cassette 28 for the open loop flow path by opening the fluid supply and drainage valves 140, 142 and circulate a pre-operative fluid through the uterus, priming the endometrial lining for ablation.

During a heating stage of the ablation procedure, the fluid from the IV bag enters the cassette 28 and is heated to a predetermined temperature (e.g., approximately 85-90° C.) as indicated by signals generated by the temperature sensors in the heating chamber 96 and transferred to the controller 44 in the console 4 via the communications board 108. The signals may be digitized and analyzed to determine when the fluid has reached the predetermined temperature. Prior to the fluid being heated, the controller 44 configures the cassette 28 for the closed loop flow path by closing the fluid supply and drainage valves 140, 142 and opening the middle valve 144 so that fluid returning from the uterus is fed back into the reservoir 92, as described above.

When the fluid has reached the predetermined temperature, the console 4 initiates a treatment stage circulating the heated fluid through the introducer 112 into the uterus to ablate the endometrial lining as described above in regard to FIG. 12. The heated fluid is delivered to the uterus via the delivery lumen in the sheath 113, removed from the uterus via the removal lumen in the sheath 113 and returned to the console 4 where it is filtered by the filter 106 and returned to be circulated through the uterus for a predetermined duration (e.g., approximately 10 minutes) to ablate the endometrial lining. The treatment stage may further include a cooling cycle in which the heated fluid is allowed to cool and then circulated through the uterus to absorb heat from the exposed tissue aiding in the healing process. When the treatment stage has been completed, the console 4 employs a drain cycle, emptying the fluid in the system into the drainage bag.

Those of skill in the art will understand that various hardware and software-based variations may be implemented in the system 5 according to the present invention. For example, the height-adjusting mechanism on the stand 8 may be controlled by position data generated by a position sensor on the introducer 112. After the introducer 112 has been inserted into the uterus, the position data may be analyzed to determined a height of the introducer above the floor. If the height of the console 4 is not properly aligned with the height of the introducer 112, an alarm may be activated or an automatic height adjusting mechanism may adjust the height of the console 4 to the desired level. In addition, a pressure transducer may be coupled to the distal end 118 of the introducer 112 to sense the fluid pressure within the uterus. The pressure transducer may provide pressure data to the controller 44 which determines whether the pressure is within a predefined operable range, and if the pressure is outside of the range, the controller 44 may execute a safety procedure.

The present invention has been described with reference to specific exemplary embodiments. Those skilled in the art will understand that changes may be made in details, particularly in matters of shape, size, material and arrangement of parts. For example, the invention is not limited to methods and devices for the thermal ablation of the uterine lining. Accordingly, various modifications and changes may be made to the embodiments. The specifications and drawings are, therefore, to be regarded in an illustrative rather than a restrictive sense.

What is claimed is:

1. A thermal ablation system, comprising:
   a fluid handling unit receiving fluid from a fluid source at a first pressure;
   an introducer including a sheath which, when in an operative position, is received within a hollow organ, the sheath including a delivery lumen and a return lumen;
   a heater configured to heat the fluid from the fluid source, the heated fluid being introduced into the hollow organ via the delivery lumen and being returned from the hollow organ to the fluid handling unit via the return lumen;
   a pump configured to increase a pressure of the fluid between the fluid source and the delivery lumen;
   a valve arrangement including a first valve configured to engage a first tube connecting the fluid handling unit to the delivery lumen, a second valve configured to engage a second tube connecting the fluid handling unit to the return lumen, and a safety valve configured to engage the first and second tubes; and
   a processor controlling an operation of the valve arrangement to deliver the fluid to the hollow organ and return the fluid from the hollow organ, the processor further configured to perform a safety procedure by activating the safety valve as a function of ablation data generated by at least one sensor.

2. The thermal ablation system of claim 1, further comprising:
   a console including a display that shows a pre-operative instruction set.

3. The thermal ablation system of claim 1, wherein the safety procedure includes shutting down the thermal ablation system.

4. The thermal ablation system of claim 1, wherein the first, second, and safety valves are pinch valves configured to close the respective tubes engaged by the first, second, and safety valves to prevent fluid flowing therethrough.

5. The thermal ablation system of claim 4, wherein the ablation data indicates the pressure of the fluid exceeds a predetermined maximum.

6. The thermal ablation system of claim 1, wherein the ablation data indicates a predetermined fault so that the processor initiates the safety procedure.

7. The thermal ablation system of claim 6, wherein the safety procedure includes a primary safety system that places the thermal ablation system in a first safe state.

8. The thermal ablation system of claim 7, wherein the safety procedure includes a secondary safety system that places the processor in a second safe state.

9. The thermal ablation system of claim 1, wherein the ablation data includes level data and the at least one sensor includes a level sensing board disposed within a reservoir that receives the heated fluid, the level sensing board generating the level data that indicates a loss of heated fluid.

10. The thermal ablation system of claim 1, wherein the ablation data includes temperature data indicating a temperature of the heated fluid, the temperature data further indicating whether the temperature of the heated fluid is within a predetermined range.

11. The thermal ablation system of claim 1, wherein the fluid handling unit further comprises:
    a reusable console including the pump; and
    a disposable cartridge including the first and second tubes and an impeller, the impeller driven by a magnetic coupling with the pump.

12. The thermal ablation system of claim 1, wherein the processor determines whether the disposable cartridge has already been used and wherein the processor initiates the safety procedure when the disposable cartridge has already been used.

13. A method for a thermal ablation system to perform a thermal ablation procedure, comprising:
    heating a fluid via a heater from a fluid source received by a fluid handling unit at a first pressure to a desired temperature;
    introducing the heated fluid in a hollow organ via a sheath including a delivery lumen of an introducer when in an operative position through a valve arrangement including a first valve configured to engage a first tube connecting the fluid handling unit to the delivery lumen;
    returning the fluid to the fluid handling unit via a return lumen of the sheath through the valve arrangement including a second valve configured to engage a second tube connecting the fluid handling unit to the return lumen;

increasing a pressure of the fluid between the fluid source and the delivery lumen of the introducer via a pump; and determining ablation data generated by at least one sensor, the ablation data indicating whether a processor is to perform a safety procedure by activating the valve arrangement including a safety valve configured to engage the first and second tubes.

14. The method of claim 13, wherein the first, second, and safety valves are pinch valves configured to close the respective tubes engaged by the first, second, and safety valves to prevent fluid flowing therethrough.

15. The method of claim 14, wherein the ablation data indicates the pressure of the fluid exceeds a predetermined maximum.

16. The method of claim 13, wherein the ablation data indicates a predetermined fault so that the processor initiates the safety procedure.

17. The method of claim 13, wherein the ablation data includes level data and the at least one sensor includes a level sensing board disposed within a reservoir that receives the heated fluid, the level sensing board generating the level data that indicates a loss of heated fluid.

18. The method of claim 13, wherein the ablation data includes temperature data indicating a temperature of the heated fluid, the temperature data further indicating whether the temperature of the heated fluid is within a predetermined range.

19. The method of claim 13, wherein the thermal ablation system comprises:

a reusable console including the pump; and a disposable cartridge including the first and second tubes and an impeller, the impeller driven by a magnetic coupling with the pump.

20. The method of claim 19, further comprising:

determining whether the disposable cartridge has already been used; and initiating the safety procedure when the disposable cartridge has already been used.

* * * * *